United States Patent [19]
Glabe et al.

[11] 4,067,999
[45] Jan. 10, 1978

[54] CONTROL OF HEMORRHAGIC ENTERITIS IN TURKEYS

[75] Inventors: Elmer F. Glabe, Northbrook, Ill.; Herbert J. Rebhan, New Richmond, Wis.

[73] Assignee: Food Technology Products, Chicago, Ill.

[21] Appl. No.: 792,695

[22] Filed: May 2, 1977

Related U.S. Application Data

[63] Continuation-in-part of Ser. No. 750,844, Dec. 15, 1976, abandoned.

[51] Int. Cl.² ............................................. A61K 31/19
[52] U.S. Cl. ................................................... 424/317
[58] Field of Search ........................................ 424/317

[56] References Cited
PUBLICATIONS

The Merck Index–Ninth Edition, (1976), p. 8345.

Primary Examiner—Sam Rosen
Attorney, Agent, or Firm—Richard L. Johnston

[57] ABSTRACT

Hemorrhagic enteritis in turkeys is controlled by adding to the drinking water used in feeding turkeys an effective amount of sodium diacetate.

3 Claims, No Drawings

CONTROL OF HEMORRHAGIC ENTERITIS IN TURKEYS

RELATED APPLICATION

This application is a continuation-in-part of U.S. patent application Ser. No. 750,844 filed Dec. 15, 1976, now abandoned.

BACKGROUND

Hemorrhagic enteritis, sometimes called "hemorrhagic syndrome" appears to be caused by a filterable agent in association with intestinal streptococci. Hemorrhagic enteritis of turkeys has been responsible for serious losses in flocks, especially in the eastern United States in recent years. The disease generally affects poults between 7 and 12 weeks of age, but some outbreaks have occurred as early as 3½ weeks and as late as 20 weeks. Generally occurring in warm weather, both range- and confinement-reared birds have developed the disease. Mortality varies but is often between 10 and 15% in a 10-day period, usually the course of the outbreak.

Signs of the disease are bloody droppings, droopy birds, and mortality. The disease can be reproduced by inoculating the turkey orally with the intestinal contents of diseased birds. The disease is recognized by a great amount of hemorrhage in the small intestine. Often, there is a ballooning of the entire intestine and its contents appear similar to strawberry jam, caused by extensive swelling and sloughing of the intestinal villi.

Insofar as is known, there is no absolute cure for the disease. Thousands of turkeys are lost every year because of the disease. Recovered flocks seems to develop antibodies in blood and blood serum from such flocks has been used with some evidence of success as a treatment when given early in the out-break of the disease. The disease runs its course in a relatively short period of time and the turkeys either die or recover but because of the short period, it is difficult to evaluate the effectiveness of an antiserum or any other treatment.

OBJECTS

One of the objects of the present invention is to provide a new and improved method of controlling hemorrhagic enteritis in turkeys which involves the simple addition of a substance to the drinking water and does not require the use of blood serum or any other substance which has to be given intramuscularly. Other objects of the invention will appear hereinafter.

BRIEF SUMMARY OF THE INVENTION

In accordance with the invention it has been discovered that the addition of a small but effective amount of sodium diacetate to the drinking water in the feeding of turkeys, either before or after the appearance of hemorrhagic enteritis in a flock, will substantially reduce mortality.

DETAILED DESCRIPTION OF THE INVENTION

Turkeys ordinarily drink relatively large amounts of water. It is, therefore, a fairly simple matter to introduce a control agent into water which is to be drunk by turkeys provided the control agent is soluble in water and the water, after its addition, is still attractive enough for the turkeys to drink it. Sodium diacetate has both of these qualifications. It has been used as an attractant in animal feeds for herbivorous animals as disclosed, for example, in U.S. Pat. No. 3,925,559. It was entirely unexpected, however, to discover that the addition of small amounts of sodium diacetate to drinking water used for turkeys would be effective to reduce mortality due to hemorrhagic enteritis.

In the practice of the invention a preferred procedure is to add a larger quantity of sodium diacetate to drinking water initially, for example, 2 pounds per 50 gallons of water, followed by a smaller quantity, for example, 1 pound per 50 gallons of water. A suitable feeding schedule appears to be the use of 2 pounds of sodium diacetate per 50 gallons of water for 2 days and then 1 pound of sodium diacetate per 50 gallons of water for 2 days or more, depending on mortality. This schedule should be followed just as soon as mortality appears in the flock. Of course, the addition of the sodium diacetate to the drinking water can be made before the disease hits the turkey flock in which case it might be possible to avoid any mortality.

A dosage of 1 pound per 50 gallons of water corresponds to 0.24% by weight of sodium diacetate. The effective dosage, therefore, appears to be within the range of 0.05% by weight to 0.5% by weight sodium diacetate.

The invention will be further illustrated but is not limited by the following examples.

EXAMPLE I

Two barns of tom turkeys of approximately the same age each having 25,000 birds were struck with hemorrhagic enteritis when they were about 8 weeks old. Barn A was treated with iodine, 5 oz. per 100 gallons of water on days 1-3, and days 6-7, from the time that the disease hit. The mortality of this flock was 1,129 birds.

The second barn hereinafter referred to as barn B was struck with the disease a few days after barn A. The birds in barn B were treated with sodium diacetate added to the drinking water at the rate of 1 pound per 500 gallons of water (0.24% by weight sodium diacetate). The mortality of this flock totaled only 42 birds over the same period of time as barn A.

EXAMPLE II

Hemorrhagic enteritis (HE) broke on the same farm as in Example I at a later date in another flock of 12,440 tom turkeys. The drinking water for the turkeys was treated with sodium diacetate added at the rate of 1 pound per 50 gallons of water. The mortality each day for the first 5 days was 9, 8, 8, 40 and 21 birds, respectively. At this time, the grower thought that the sodium diacetate was not doing any good so he stopped using it and mortality on day 6 climbed to 45 and on day 7 to 96 birds. On days 8 and 9 the birds were put on sulfa quinoxilene. The mortality was 83 birds for day 8 and 114 birds for day 9. The birds were again put back on sodium diacetate added to the drinking water at the rate of 1 pound per 50 gallons of water. The mortality decreased to 88 birds for day 10 and 49 birds for day 11. After this, the mortality continued to decrease.

EXAMPLE III

A flock of 20,240 turkeys 8 weeks old were hit with hemorrhagic enteritis and the mortality the first day was 119 birds. The remainder of the flock was immediately treated with sodium diacetate by adding it to the drinking water at the rate of 1 pound per 25 gallons of water (0.48% by weight sodium diacetate) for 48 hours.

Mortality decreased to 39 birds and 18 birds. Then the drinking water was treated with 1 pound of sodium diacetate per 50 gallons of water (0.24% by weight sodium diacetate) and mortality dropped even further to 11 birds one day and 4 birds the next day.

At about this time, a flock of 71,093 turkeys in another building was struck with hemorrhagic enteritis. The drinking water for these birds was treated with sodium diacetate added at the rate of 1 pound per 25 gallons of water for 48 hours and then 1 pound per 50 gallons of water for 48 hours. The daily mortality on successive days was 15, 9, 5 and 2 birds, respectively.

EXAMPLE IV

A flock of turkey hens was hit with hemorrhagic enteritis after 11 weeks and 6 days. On the first day that the disease struck two birds died. The addition of sodium diacetate to the drinking water was started immediately at the rate of 2 pounds of sodium diacetate per 50 gallons of water on the first day and 1 pound of sodium diacetate per 50 gallons of water on the second, third, fourth and fifth days. The mortality on the second, third, fourth and fifth days was 18, 4, 4, and 5 birds, respectively. On the sixth and seventh days the mortality was 3 birds each day and on the eighth day the mortality was 3 birds and the flock was sent to market. A total of 10,802 birds were shipped to the processing plant. The birds were marketed as fryers at an average weight of 9.6 pounds and 88.6% graded A, which was excellent. Only 28 were condemned which was also excellent.

It is apparent from the foregoing examples that the addition of the sodium diacetate to the drinking water was effective in controlling hemorrhagic enteritis and in improving the health of the turkeys. The use of sodium diacetate for this purpose is very advantageous because it is a relatively inexpensive substance that is known to be non-toxic in the amounts which are effective for the purpose of the invention, and it is quite simple to use because it is readily soluble in the drinking water. In contrast, the other types of control which have been attempted such as the use of blood serum from flocks that have recovered, require intramuscular injection which is a difficult method of treatment. Moreover, as shown by the foregoing examples, the use of antiseptic agents such as iodine added to the drinking water, has not been particularly effective. It is believed to be self-evident from the foregoing tests as set forth in the examples that sodium diacetate added to drinking water for turkeys is a powerful inhibitor of the organism or virus causing hemorrhagic enteritis.

The invention is hereby claimed as follows:

1. A method of controlling hemorrhagic enteritis in turkeys which comprises adding to the drinking water an effective dosage of sodium diacetate.

2. A method as claimed in claim 1 in which the dosage of sodium diacetate is within the range of 0.05% to 0.5% by weight of the drinking water.

3. A method as claimed in claim 1 in which the sodium diacetate is added to the drinking water just as soon as practical after hemorrhagic enteritis strikes at a rate of about 2 pounds of sodium diacetate per 50 gallons of water for a period of at least 2 days followed by a reduced dosage of about 1 pound of sodium diacetate per 50 gallons of water on successive days until mortality has been reduced to a minimum.

* * * * *

UNITED STATES PATENT AND TRADEMARK OFFICE
CERTIFICATE OF CORRECTION

PATENT NO. : 4,067,999
DATED : January 10, 1978
INVENTOR(S) :

It is certified that error appears in the above—identified patent and that said Letters Patent are hereby corrected as shown below:

Col. 2, line 40, "500" should read --50--.

Signed and Sealed this

Thirtieth Day of May 1978

[SEAL]

Attest:

RUTH C. MASON
Attesting Officer

LUTRELLE F. PARKER
Acting Commissioner of Patents and Trademarks